United States Patent [19]
Presby

[11] 4,168,907
[45] Sep. 25, 1979

[54] METHOD FOR INSPECTING TRANSPARENT RODS

[75] Inventor: Herman M. Presby, Highland Park, N.J.

[73] Assignee: Bell Telephone Laboratories, Incorporated, Murray Hill, N.J.

[21] Appl. No.: 865,977

[22] Filed: Dec. 30, 1977

[51] Int. Cl.² ............................................. G01N 21/32
[52] U.S. Cl. .................................. 356/73.1; 356/239
[58] Field of Search ............... 356/239, 107, 111, 73.1

[56] References Cited
U.S. PATENT DOCUMENTS

| | | | |
|---|---|---|---|
| 3,777,171 | 12/1973 | Hollenbeck | 356/239 |
| 3,879,128 | 4/1975 | Presby | 356/107 |
| 3,980,890 | 9/1976 | Heckrodt et al. | 356/239 |
| 4,021,217 | 5/1977 | Bondybey et al. | 356/239 |
| 4,027,977 | 6/1977 | Frazee, Jr. et al. | 356/111 |
| 4,042,723 | 8/1977 | Presby | 356/107 |

*Primary Examiner*—Vincent P. McGraw
*Attorney, Agent, or Firm*—Sylvan Sherman

[57] ABSTRACT

A sensitive, nondestructive method of viewing the internal structure of multilayered optical fiber preforms is described. The method comprises the steps of transversely illuminating the preform, and intercepting the light that traverses the preform on a viewing screen. To obtain a complete picture, the preform is rotated 360 degrees about its axis. The technique provides a detailed view of the core size and eccentricity, and of the structure of the multilayered core.

6 Claims, 10 Drawing Figures

METHOD FOR INSPECTING TRANSPARENT RODS

TECHNICAL FIELD

This invention relates to a method for examining preforms from which optical fibers are drawn.

BACKGROUND ART

Preforms, from which step index and graded index optical fibers are drawn, can be manufactured in any one of a variety of ways. One such way is the so-called "modified chemical vapor deposition" (MCVD) process in which a plurality of layers of suitably doped silicate glasses are deposited on the inside of a fused silica tube. After the requisite number of layers (i.e., typically about 50), have been deposited, the tube is collapsed into a solid rod which constitutes the preform from which a fiber can be drawn. For a more detailed discussion of the MCVD process, see the article by J. B. MacChesney, Chesney, P. B. O'Connor and H. M. Presby entitled "A New Technique for the Preparation of Low-Loss and Graded-Index Optical Fibers," published in the *Proceedings of the IEEE*, pp. 1278-1279. Also see, "Preparation and Structural Characteristics of High Silica, Graded Index Fibers" by P. B. O'Connor, J. B. MacChesney, H. M. Presby and L. G. Cohen, published in *The American Ceramic Society Bulletin*, Vol. 55, No. 5, May 1976, pp. 513-519.

After the preform is made, the fiber is drawn and tested. While it would be reasonable to assume that fibers drawn from preforms fabricated in substantially the same manner would exhibit similar characteristics, this has not always been the case. Indeed, it is not unusual for lengths of fibers drawn from different portions of the same preform to have significantly different transmission characteristics. Unfortunately, some lengths of fibers are totally unusable and must be discarded.

While the ultimate cost of mass produced optical fibers can only be guessed at this time, it is known that the cost of pulling the fiber from the preform, coating it and then testing it might be anywhere between 30 and 50 percent of the total cost of the fiber. It is apparent, therefore, that a significant saving could be realized if there was some simple and convenient way of examining the preform before the fiber is drawn to determine whether or not a usable fiber is likely to be produced.

Techniques for inspecting glass rods for gross defects are well known. In U.S. Pat. Nos. 3,777,171 glass tubing is inspected for flaws by directing a pair of narrow band, high intensity laser beams, spaced 90 degrees from each other about the axis of the tubing, through the tubing. Changes in the intensity of the transmitted light are detected by a pair of photodetectors, thus providing an indication of the presence and location of a flaw.

U.S. Pat. No. 4,021,217 discloses a method of inspecting optical fibers for surface cracks. In particular, light that is scattered out of the plane normal to the fiber axis is monitored by means of a photodetector. When defects are detected, the fiber drawing process is terminated.

Neither of these patents, however, is concerned with, or discloses means for examining the internal structure of a glass rod and, in particular, of optical fiber preforms.

SUMMARY OF THE INVENTION

The present invention is based upon the recognition that notwithstanding the fact that an optical fiber preform can include one or a plurality of layers of the same or of different refractive index materials, it is nevertheless possible to view each of the layers and determine its uniformity, or lack of uniformity, over the entire length of the preform, and to detect the presence of internal defects, such as bubbles. This is accomplished, in accordance with the present invention, by a process that includes the steps of transversely illuminating the preform along at least a portion of its length, and intercepting the light that traverses the preform on a viewing screen. In addition, the preform can be rotated about its axis as a means of viewing the entire periphery of each layer.

The ability to view, in great detail, the structure of the deposited layers provides an immediate means for evaluating the preform and predicting the usability of the fiber that might be drawn from it. In addition, the process provides a means for identifying those portions of the preform which are usable and those which are unusable. It provides a simple and immediate means of determining the effect upon the preform of changes in the preform fabrication process without the need of drawing a fiber from the preform. The resulting savings in both time and money that can be realized by the present invention are, therefore, readily apparent.

IN THE DRAWINGS

DETAILED DESCRIPTION

Figure 1:
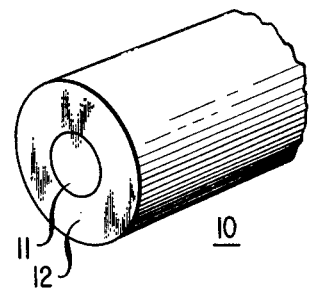
FIG. 1 shows an optical fiber preform including an inner core region surrounded by a cladding.

Referring to the drawings, FIG. 1 shows a portion of an optical fiber preform 10 comprising an inner core region 11 surrounded by an outer cladding 12 of lower refractive index material. The core can be made of a homogeneous material having a constant refractive index, or it can be fabricated by depositing a plurality of layers of material of the same or different refractive indices to produce either a step index or graded index preform.

Figure 2:
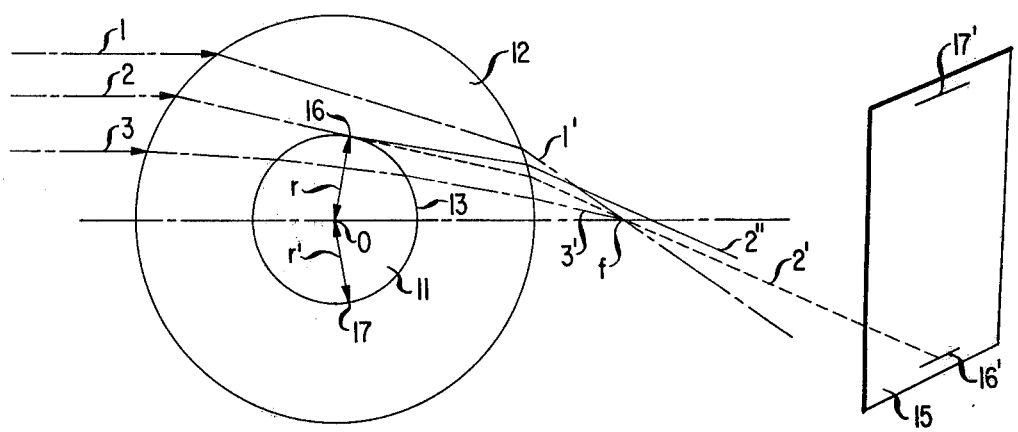
FIG. 2 shows the paths taken by light rays of a transversely illuminated preform.

Whatever process is used to fabricate the preform the fiber that can be drawn from it will be no better than the preform itself. See, for example, the article by H. M. Presby et al entitled "Material Structure of Germanium-Doped Optical Fibers and Preforms" published in the Dec. 1975 *Bell System Technical Journal*, Vol. 54, No. 10, pp. 1681-1692. Accordingly, it is essential that some means be devised to inspect the preform to determine its internal structure. To this end, it will be shown that transverse illumination of the preform rod can give a clear and detailed picture of the core-cladding interface, and of the refractive index striations within the core itself. For purposes of explanation, let us now consider preform 10 transversely illuminated as shown in FIG. 2 by means of a light source not shown. The nature of the light source is not important in that it can be either a white light source or a monochromatic light source.

In general, those light rays that are intercepted by the preform are caused to converge at a focal point f due to the focusing action of the rod. More specifically, an outer ray, such as ray 1, is refracted in the usual manner as it enters the cladding region and, again, as it leaves the cladding in the direction indicated by ray 1'. Similarly, a ray 3, closer to the center of the preform, is refracted at the interface of the cladding and the surrounding air as it enters and leaves the preform as ray 3'. In addition, it is refracted at the core-cladding interface as it traverses the rod. Between those rays that traverse only the cladding, typified by ray 1, and those rays that traverse both the core and the cladding, typified by ray 3, there is a particular group of ways, typified by a ray 2 which, after being refracted at the air-cladding interface at it enters the cladding, is incident at the core-cladding interface at a grazing angle and is totally reflected. These rays, instead of emerging from the preform along a path indicated by dotted line 2', follow a slightly different path 2''. As a result, the output light that would have been contributed by output ray 2' is missing, giving rise to a dark region which can be clearly seen on a viewing screen 15, shown in perspective in FIG. 2. Located beyond the focal point f, a lower dark line 16' will be seen on the screen due to the reflection of ray 2 at a point 16 along the core-cladding interface. Similarly, an upper dark line 17' will also be seen due to the reflection of a corresponding ray at a point 17 along the core-cladding interface.

The balance of screen 15 will be illuminated by the refracted light rays typified by rays 1' and 3', and by those rays which were not intercepted by the preform. Thus, the total overall picture, as viewed on screen 15, will include a level of background illumination, a shadow of preform 10, and the two dark lines 16' and 17' whose location will depend upon the distance between the preform and the screen and the distances r and r' between the center of the preform 0 and points 16 and 17 along the core-cladding interface. In the usual case, the core region is symmetrically disposed about the longitudinal axis of the preform so that r = r'. Whether this is so can readily be observed, in accordance with the teachings of the present invention, by simply rotating the preform about its longitudinal axis. If, indeed, the core region is circular and coaxial with the preform, the positions of dark lines 16' and 17' will not change as the preform is rotated. If however, there is any axial asymmetry in the core, the relative positions of the dark lines will change. Similarly, any asymmetry in the core along the length of the preform can readily be observed by observing the relative positions of the dark lines as different regions along the length of the preform are illuminated.

Figure 3:
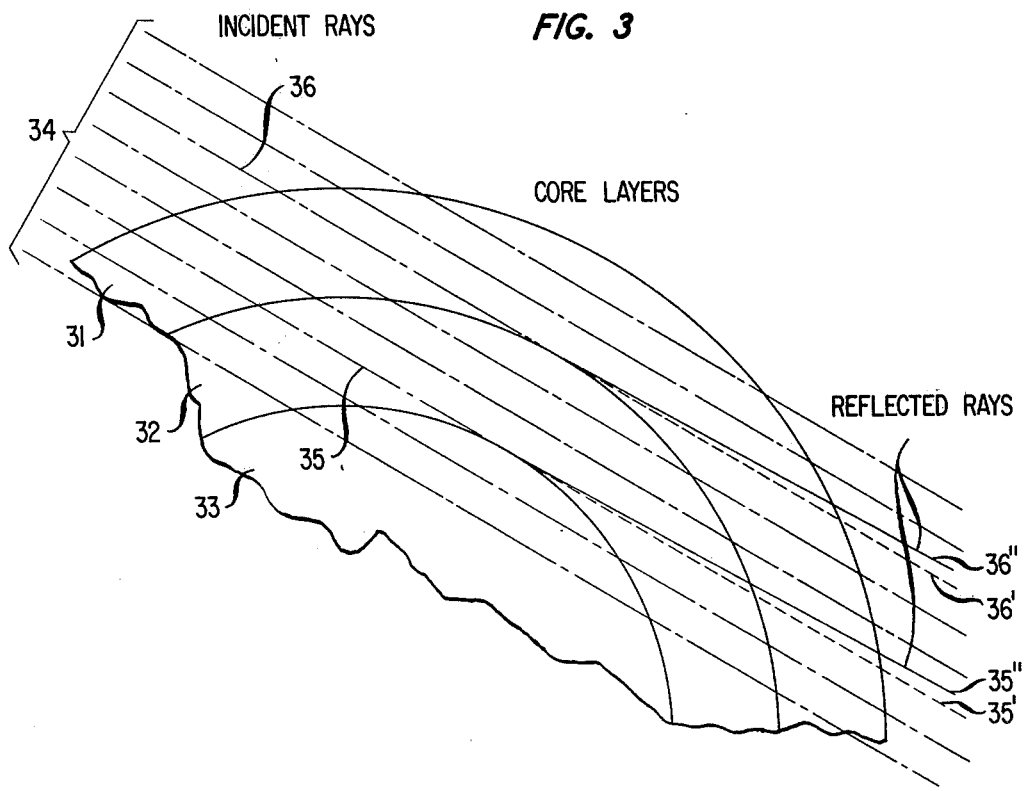
FIG. 3 shows, in greater detail, the paths taken by light rays as they traverse a multilayered preform.

The underlying principal described hereinabove is equally applicable as a means of revealing the internal structure of a multilayered core. FIG. 3, now to be considered, shows a portion of a core including four adjacent layers 30, 31, 32 and 33, and a plurality of incident rays 34. Most of these rays propagate through the various layers, experiencing some slight refraction at each layer-to-layer interface. However, those particular rays, such as rays 35 and 36, that are incident at the layer-to-layer interfaces at a grazing angle are reflected and follow along the directions indicated by rays 35'' and 36'', respectively, instead of along the directions indicated by dotted lines 35' and 36'. As a result, a dark line appears on the viewing screen for each interface between adjacent layers.

Figure 4:
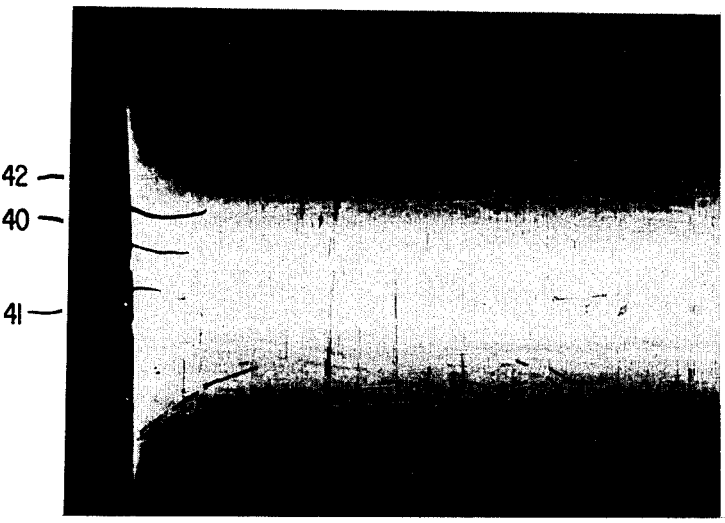
FIGS. 4, 5, 6 and 7 are photographs of preforms made in accordance with the present invention.

FIG. 4 is a view of a portion of a "homogeneous" rod showing a bright area 40 of general background lighting caused by that portion of the incident light that did not traverse the rod, and the shadow 41 cast by the rod. The pattern of light and dark regions 42 are caused by defects in the rod which tend to scatter the light that traverses the rod.

Figure 5:
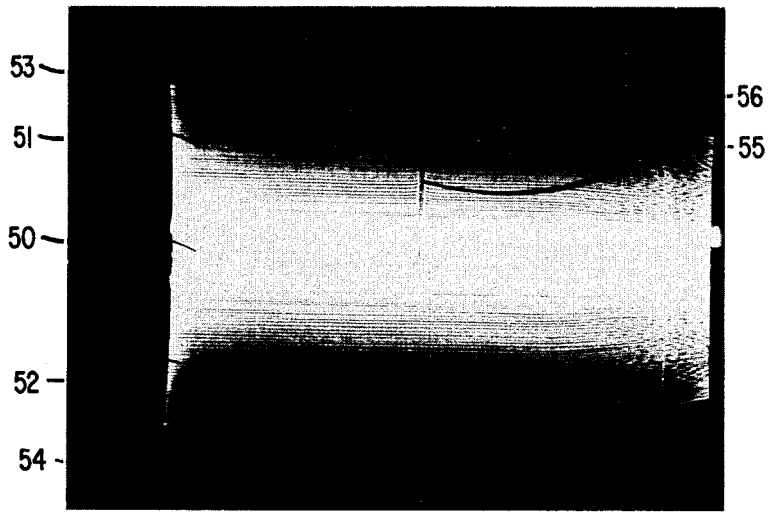

FIG. 5 is a view of a portion of a preform fabricated by the MCVD process described hereinabove. The photograph shows background light and shadow area 50 and the bright and dark regions 51 and 52 showing each of the layers which make up the core region. It should be noted, however, that this one pattern reveals the layer geometry for only a specific rotational orientation of the preform, and essentially indicates what would be observed if the preform was cut along an axial plane perpendicular to the direction of the incident light and its interior structure exposed. To reveal the complete layer geometry, the preform is rotated 360 degrees about its longitudinal axis.

In addition, FIG. 5 also shows a pair of bright lines 53 and 54 which define the core-cladding interface, and a dark region 55 which identifies a defect in the preform. To determine whether the defect is in the core region or in the cladding, the preform is rotated 360° about its axis, causing the dark region 55 to move up and down. If the dark region remains between the bright lines 53 and 54 as it moves up and down, the defect is within the core. If, on the other hand, it moves beyond lines 53 and 54, the defect is in the cladding.

The pattern of bright and dark lines to the left of defect 55 and immediately to the right of the defect are seen to be uniform. Further to the right, the layers enter a transition region 56 where they taper down and become irregular.

It is evident from FIG. 5 that this particular preform should only be pulled up to the defect 55. Any fiber drawn from the defective region would clearly be unusable. Similarly, any fiber pulled from the transition region would also be defective. Thus, an inspection of a preform in accordance with the present invention would immediately indicate the usable portions of the preform, resulting in a considerable saving in time and money.

Figure 6:
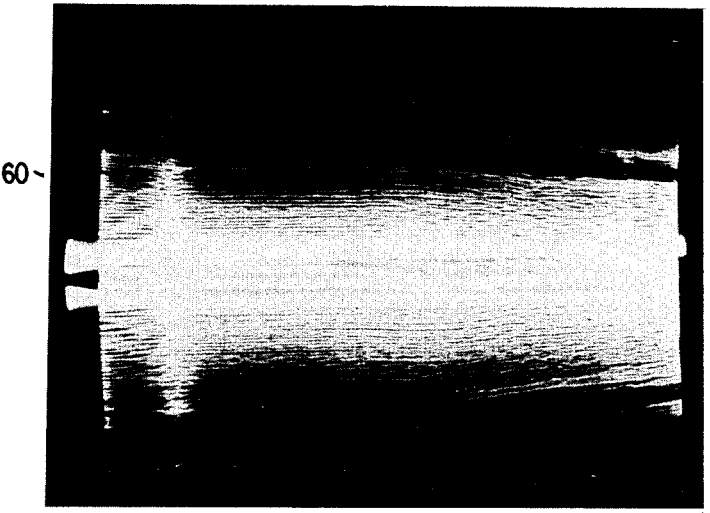

FIG. 6 shows a portion of a preform in which the layer pattern 60 is immediately seen to be irregular, and would suggest that the fiber drawn from such a preform would be of less than optimum quality.

Figure 7:
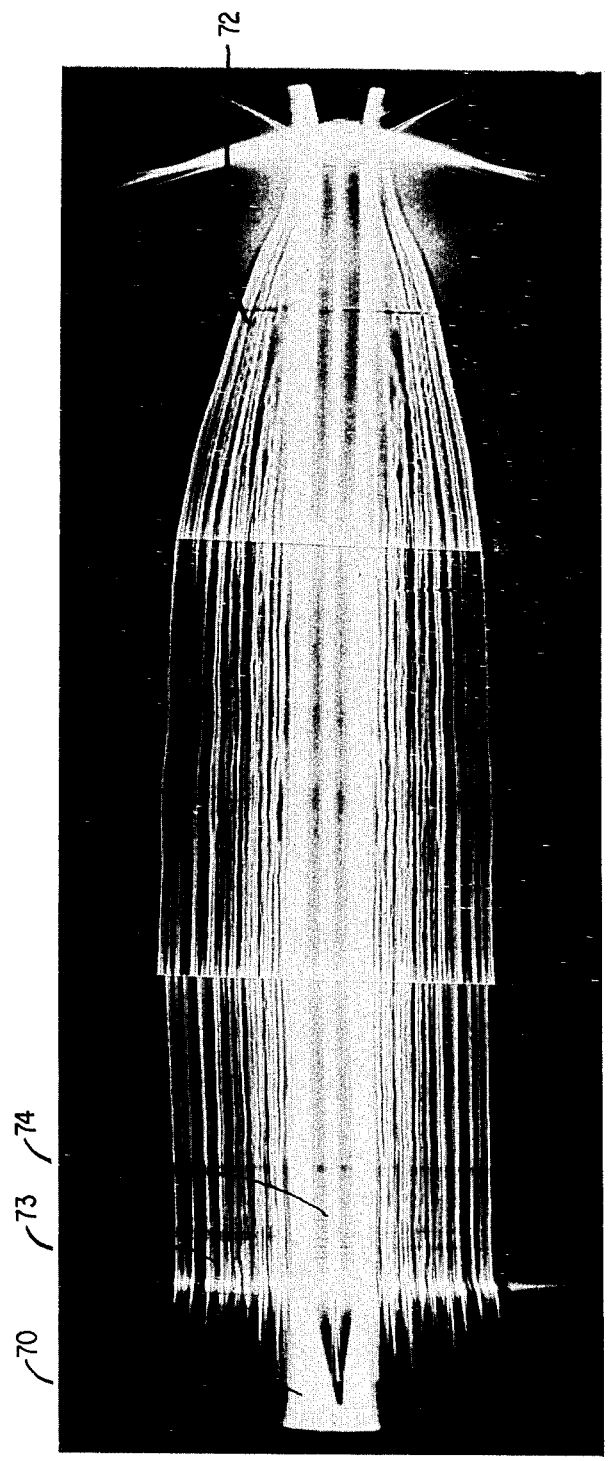

FIG. 7 is a view of a 40 cm section of a preform made up of three photographs clearly showing all of the features typically obtained in accordance with the present invention including the background lighting 70, the shadow 71, the end transition region 72, and the bright and dark line pattern of the core layers 73. Also shown in the central region of the preform shadow is a double line pattern 74. This pattern is caused by a refractive index depression which exists along the preform axis and is due to the evaporation of dopant caused by the relatively high temperatures produced in the preform when it is collapsed.

Figure 8:
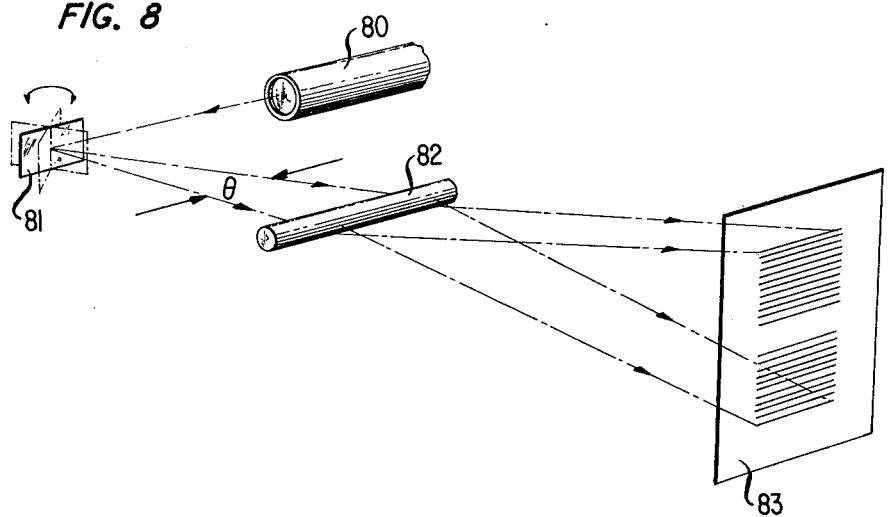
FIGS. 8 and 9 show two arrangements for viewing the internal structure of optical fiber preforms.

FIG. 8 shows one arrangement for examining preforms in accordance with the present invention. Light, from a light source 80, is directed onto an oscillating mirror 81 which deflects the incident beam through an arc of $\phi$ degrees, sufficient to scan all or whatever portion of the preform 82 is to be viewed. Optical focusing means, not shown, are advantageously employed to control the size of the incident beam so as to minimize the area of background lighting incident upon viewing screen 83. By minimizing the background lighting the details of the preform can be more clearly observed.

In operation, the test preform to be examined is inserted into the region of the light beam so as to be illuminated along its length. The light that traverses the preform is then viewed on the viewing screen. To obtain a complete picture of the preform, the latter is rotated about its longitudinal axis.

It should be noted that there are no special requirements imposed upon the light source. It can be either a coherent, monochromatic source or an incoherent, white light source. All that is required is that the source be sufficiently bright to show the preform structure clearly enough for the particular application at hand.

It should also be noted that the magnification with which the bright and dark line pattern is viewed can be easily changed simply by moving the viewing screen towards or away from the preform.

Figure 9:
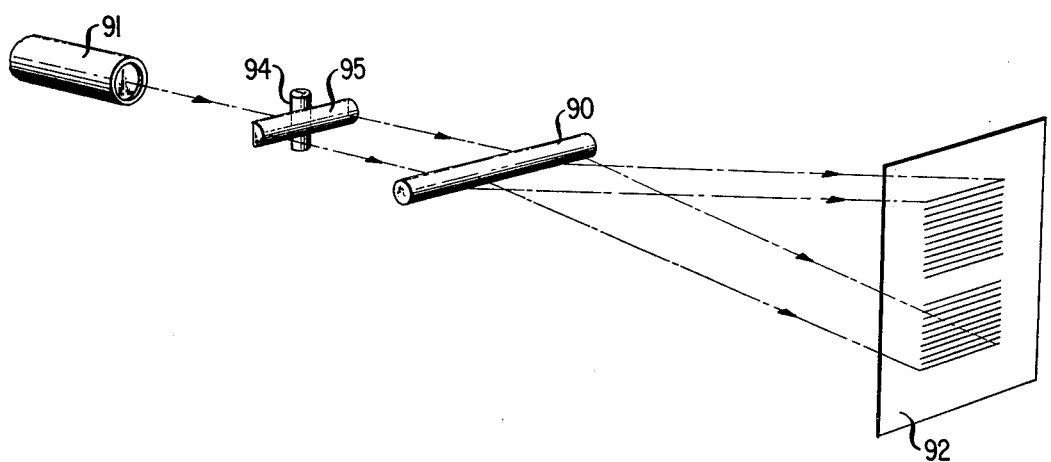

FIG. 9 is an alternative arrangement for viewing the internal structure of a preform wherein a lens system is substituted for the oscillating mirror. As before, a preform 90 is illuminated along its length by light from a source 91, and the light that traverses the preform is viewed on a viewing screen 92. In this embodiment, a thin, flat beam is produced by means of a composite lens 93 comprising a rod 94 which serves to spread the beam in a first direction normal to the rod axis, and a plane cylindrical lens 95 which serves to spread the beam in a direction perpendicular to the first direction. In all other respects, the embodiment of FIG. 9 operates in the manner described in connection with the embodiment of FIG. 8.

SUMMARY

A sensitive, nondestructive and noncontacting method of obtaining structural information about preforms from which optical fibers are produced has been described. The technique permits a determination of the size and eccentricity of the core region of the preform from direct observations of light that has traversed the preform along a direction normal to its longitudinal axis. Also observable are the core-cladding interface structure; the individual layers that comprise the core; and imperfections within the core and cladding. An analysis of the light pattern yields quantitative data of the refractive index profile of the core.

APPENDIX

In the description of the invention given hereinabove, generally qualitative information about the test preforms are discussed. The purpose of this appendix is to describe how quantitative information can also be derived from the light pattern generated in accordance with the present invention.

As was explained in connection with FIGS. 2 and 3, the forward scattered light field includes bright and dark lines, each of which provides different information. More specifically, the width of the bright lines is indicative of the physical width of the individual core layers, as measured by the discontinuous refractive index increments of each layer. The width of the dark lines, on the other hand, is indicative of the difference in the refractive index of adjacent layers.

Figure 10:
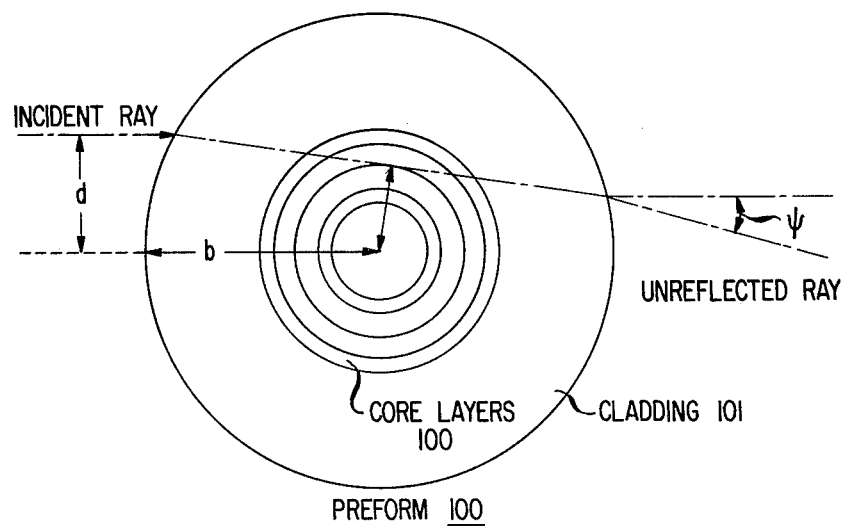
FIG. 10, included for purposes of explanation and analysis, shows a multilayered preform.

FIG. 10, now to be considered, shows the cross section of a preform 100 comprising a cladding 101 surrounding a multilayer core 102. As a practical matter, the refractive index differences between adjacent layers is so small that a light ray traversing the core is deflected very little by the gradient of the refractive index function n(r). However, because of the discrete discontinuity in the refractive index at each layer-to-layer interface, a ray incident to the discontinuity at a sufficiently small grazing angle $\Phi$ will be totally reflected and will be displaced in the field of output rays, giving rise to a dark line. Thus, the positions of the dark lines are related to the thicknesses of the layers.

The angle $\psi$ through which an unreflected ray is refracted as it traverses the preform is given by $$\psi = 2\left[\arcsin\frac{d}{b} - \arcsin\frac{d}{nb}\right] \qquad (1)$$

where
d is the distance between the incident ray and the center of the preform;
b is the radius of the preform; and
n is the refractive index of the preform cladding.
Solving equation (1) for d yields $$d = \frac{nb \sin\left(\frac{\psi}{2}\right)}{\left[(n^2 + 1) - 2n \cos\frac{\psi}{2}\right]^{\frac{1}{2}}} . \qquad (2)$$

Applying Snell's law and elementary geometry, the radius r can be expressed as $$r = d/n \qquad (3)$$

Substituting d/n for r in equation (2), we obtain $$r = \frac{b \sin\left(\frac{\psi}{2}\right)}{\left[(n^2 + 1) - 2n \cos\frac{\psi}{2}\right]^{\frac{1}{2}}} \qquad (4)$$

Thus, by measuring the angle $\psi$ at the position of a dark line, the radius of the index discontinuity can be calculated, and in turn, the thickness of each layer determined.

It is also possible to estimate the magnitude of the index discontinuity $\Delta n$ by measuring the angle $\Delta \psi$ subtended by the dark line. As explained hereinabove, the dark line is caused by the reflection of a ray incident at a grazing angle at an index discontinuity. For very small angles $\Phi$ between a ray and the tangent to the index continuity, the power reflection coefficient R can be expressed as $$R = \left[\frac{n\Phi - \sqrt{2n\Delta n}}{n\Phi + \sqrt{2n\Delta n}}\right]^2 \qquad (5)$$

For $\Phi = 0$, we obtain $R = 1$. However, R decreases rapidly as $\Phi$ increases, and is zero for $$\Phi = \sqrt{\frac{2\Delta n}{n}}. \quad (6)$$

Equation (1) permits us to relate the change $\Delta\psi$ to a corresponding change $\Delta d$ in d. If we relate the change $\Delta d$ in the input way that causes $\Phi$ to change from zero to the value given by equation (6), the following relation between the angular width $\Delta\psi$ of a dark line, and the refractive index difference $\Delta n$ is obtained:

$$\frac{\Delta n}{n} = \frac{(n\cos\frac{\psi}{2} - 1)(n - \cos\frac{\psi}{2})}{2(n^2 - 2n\cos\frac{\psi}{2} + 1)\sin\frac{\psi}{2}} \Delta\psi. \quad (7)$$

For small values of $\psi$, equation (7) reduces to $$\Delta n/n = \Delta\psi/\psi. \quad (8)$$

It should be noted that while equation (5) was derived under the assumption that the refractive index increases towards the center of the preform, equation (6) remains unchanged if, in fact, the index step represents a decrease in the refractive index.

What is claimed is:

1. A method of viewing the internal structure of transparent rods, comprising at least two layers of different refractive index material, including the steps of:
   transversely illuminating the length of rod to be viewed;
   intercepting the light that traverses said rod on a viewing screen for displaying a picture of the internal structure of said rod.

2. The method according to claim 1 wherein said rod is an optical fiber preform having a multilayered core region.

3. The method according to claim 2 wherein said layers have different refractive indices.

4. The method according to claim 1 including the step of rotating said rod about its longitudinal axis.

5. The method according to claim 1 wherein the illuminating light is derived from a coherent source.

6. The method according to claim 1 wherein said illuminating light is derived from an incoherent light source.

* * * * *